United States Patent [19]

Figuly

[11] Patent Number: 5,667,774
[45] Date of Patent: Sep. 16, 1997

[54] CROSSLINKED POLYMERIC AMMONIUM SALTS

[75] Inventor: Garret Daniel Figuly, Wilmington, Del.

[73] Assignee: E.I. Du Pont de Nemours and Company, Wilmington, Del.

[21] Appl. No.: 746,259

[22] Filed: Nov. 7, 1996

Related U.S. Application Data

[60] Division of Ser. No. 381,876, Feb. 17, 1995, which is a continuation-in-part of Ser. No. 932,449, filed as PCT/US93/07647, Aug. 18, 1993, published as WO94/04596 Mar. 3, 1994, abandoned.

[51] Int. Cl.$^6$ .................................................. A61K 31/74
[52] U.S. Cl. ................. 424/78.08; 528/373; 528/397; 528/422; 424/719; 424/721; 424/723; 514/63; 514/553; 514/556; 514/579; 514/642; 514/788; 514/964
[58] Field of Search .................................... 528/373, 397, 528/422; 424/78.08, 719, 721, 723; 514/63, 553, 556, 579, 642, 788, 964

[56] References Cited

U.S. PATENT DOCUMENTS

| | | | |
|---|---|---|---|
| 3,332,841 | 7/1967 | Ainsworth et al. | 424/183.7 |
| 3,383,281 | 5/1968 | Wolf et al. | 167/65 |
| 3,692,895 | 9/1972 | Nelson et al. | 424/78 |
| 3,980,770 | 9/1976 | Ingelman | 424/78.1 |
| 4,027,009 | 5/1977 | Grier et al. | 424/78 |
| 4,071,478 | 1/1978 | Shen et al. | 260/2 R |
| 4,147,586 | 4/1979 | Petrovich et al. | 162/135 |
| 4,205,064 | 5/1980 | Wagner et al. | 424/78 |
| 4,374,244 | 2/1983 | Green et al. | 542/476 |
| 4,775,384 | 10/1988 | Bachem et al. | 8/115 |
| 5,114,709 | 5/1992 | St. Pierre et al. | 424/78.12 |
| 5,236,701 | 8/1993 | St. Pierre et al. | 424/78.12 |

FOREIGN PATENT DOCUMENTS

| | | |
|---|---|---|
| 0081291 | 6/1983 | European Pat. Off. . |
| 2441639 | 6/1980 | France . |
| 2427924 | 1/1975 | Germany . |

OTHER PUBLICATIONS

DeSimone, R. et al, *Journal of Pharmaceutical Sciences*, 67, 1695–1698, 1978.

Dick, C. R. et al, *J. Macromal Sci.–Chem.*, A4(6), 1301–1314, Oct. 1970.

*Primary Examiner*—Samuel A. Acquah

[57] ABSTRACT

Disclosed are novel crosslinked polymeric ammonium salts wherein in said salt: about 25% or more of the groups which link ammonium nitrogen atoms are group Y wherein Y is an-alkylene groups or alkyl substituted n-alkylene group, wherein said n-alkylene group has 7 to about 20 carbon atoms; zero to about 75% of groups which links ammonium nitrogen atoms are group Z wherein Z is a hydrocarbylene radical containing 2 or more carbon atoms, said hydrocarbylene radical optionally containing one or more hydroxyl, ether, amino, thioether, keto, or silyl groups or heterocyclic rings; and about 25% or more of the ammonium atoms are secondary ammonium atoms.

16 Claims, No Drawings

CROSSLINKED POLYMERIC AMMONIUM SALTS

This case is a division of Ser. No. 08/381,876, filed nationally in the United States on Feb. 17, 1995, which is a 35 USC 371 of PCT/US93/07647, filed on Aug. 18, 1993, published as WO94/04596 Mar. 3, 1994, which is a continuation-in-part of Ser. No. 07/932,449 filed on Aug. 20, 1992, now abandoned.

FIELD OF INVENTION

This invention concerns novel, crosslinked polymeric ammonium salts. Uses for these compositions are as absorbents, electroconductive agents, charge transfer agents, chelating agents and ion exchange resins. These salts are also useful as bile acid sequestrants, i.e., when administered orally, the polymers lower blood cholesterol levels in mammals.

TECHNICAL BACKGROUND

U.S. Pat. No. 4,071,478 describes the use of crosslinked polymers containing quaternary ammonium groups in the polymer backbone which are separated by trimethylene groups. No mention is made of the use of polymers containing ammonium salts which are not quaternary ammonium salts.

U.S. Pat. No. 4,775,384 describes the reaction of various organic compounds containing two halogen groups with various diamines to form polymeric ammonium salts. These salts are described as water soluble, and are thus not crosslinked. After further reactions, they are described as being useful as fiber finishes.

U.S. Pat. No. 4,147,586 describes the reaction of certain dihaloalkanes with alkylene diamines to form "adducts" which are water soluble. The adducts are useful, after reaction with an epihalohydrin, for increasing the wet strength of paper.

Several different types of bile acid sequestrants are known. Some of these are polymers which contain ammonium salts (amine groups in the salt form) which are bound to or are part of a polymer molecule. Such polymers vary in their ability to bind bile acids, their toxicity and their ease of administration. Thus, improved bile acid sequestrants are still being sought.

U.S. Pat. No. 3,383,281 describes the use of crosslinked polymers containing amine groups as bile acid sequestrants. In particular, the use of crosslinked styrenes containing quaternary ammonium groups is described. Such resins, which are also useful as ion exchange resins, are believed to be the active ingredient in the commercially available cholestyramine which is used to lower blood cholesterol levels.

U.S. Pat. No. 4,027,009 describes the use of linear (not crosslinked) polymers containing quaternary ammonium groups in the polymer backbone as bile acid sequestrants. The nitrogen atoms of the polymer are connected by methylene chains of designated size, or other designated groups. No mention is made in this patent of the use of crosslinked polymers (except as background information), or the use of polymers containing ammonium salts that are not quaternary ammonium salts.

SUMMARY OF THE INVENTION

This invention includes crosslinked polymeric ammonium salts, useful as bile acid sequestrants, as absorbents or as charge transfer agents, wherein in said salts:

- about 25% or more of the groups which link ammonium nitrogen atoms are group Y wherein Y is an n-alkylene group or alkyl substituted n-alkylene group, wherein said n-alkylene group has 7 to about 20 carbon atoms;
- zero to about 75% of the groups which link ammonium nitrogen atoms are group Z wherein Z is a hydrocarbylene radical containing 2 or more carbon atoms, preferably 2 to 50 carbon atoms, said hydrocarbylene radical optionally containing or substituted with one or more hydroxyl, ether, amino, thioether, keto, ester, silyl group or heterocyclic rings; and
- about 25% or more of the ammonium nitrogen atoms are secondary ammonium nitrogen atoms.

This invention further concerns a method for lowering blood plasma cholesterol levels of mammals, comprising, orally administering a therapeutically effective amount of a crosslinked polymeric ammonium salt, wherein in said salt;

- about 25% or more of the groups which link ammonium nitrogen atoms are group Y, wherein Y is an n-alkylene group or alkyl substituted n-alkylene group, wherein said n-alkylene group has 7 to about 15 carbon atoms;
- zero to about 75% of the groups which link ammonium nitrogen atoms are group Z wherein Z is a hydrocarbylene radical containing 2 or more carbon atoms, preferably 2 to 50 carbon atoms, said hydrocarbylene radical optionally containing or substituted with one or more hydroxyl, ether, ester, amino, thioether, keto, silyl group or heterocyclic rings; and
- about 25% or more of the ammonium nitrogen atoms are secondary ammonium nitrogen atoms.

This invention includes a method for sequestering bile acids, comprising, contacting in an aqueous medium a bile acid and a crosslinked polymeric ammonium salt, wherein in said salt:

- about 25% or more of the groups which link ammonium nitrogen atoms are group Y wherein Y is an n-alkylene group or alkyl substituted n-alkylene group, wherein said n-alkylene group has 7 to about 15 carbon atoms;
- zero to about 75% of the groups which link ammonium nitrogen atoms are group Z wherein Z is a hydrocarbylene radical containing 2 or more carbon atoms, preferably 2 to 50 carbon atoms, said hydrocarbylene radical optionally containing or substituted with one or more hydroxyl, ether, ester, amino, thioether, keto, silyl group or heterocyclic rings; and
- about 25% or more of the ammonium nitrogen atoms are secondary ammonium nitrogen atoms.

In the above defined embodiments, it is preferred if substituents on the hydrocarbylene contain 1 to 50 carbon atoms, more preferably 1 to 30 carbon atoms.

Included in the present invention are pharmaceutically acceptable salts and prodrugs of the above described crosslinked polymeric salts.

DETAILS OF THE INVENTION

The materials used and described herein are crosslinked polymeric ammonium salts. By crosslinked is meant a polymer which has a network structure. A common test to determine if a polymer is crosslinked is to try to dissolve the polymer in a liquid that is normally a solvent for that polymer. Linear or branched, but not crosslinked, polymers will dissolve in the solvent. Crosslinked polymers do not dissolve, although they may swell to some degree. The polymeric ammonium salts described herein, when not crosslinked, are generally soluble in water or other polar solvents. When crosslinked, the polymeric ammonium salts swell in water, often to form gel-like materials.

For use as a bile acid sequestrant or for lowering blood plasma cholesterol levels the crosslinked polymeric ammonium salts of this invention may be used in dry or nearly dry form or swollen in water. It is preferred if the polymeric ammonium salt used has a swell factor of at least about 4, preferably about 5 to 25 and more preferably about 10 to 15. The swell factor is taken as the ratio of the weight of water imbibed by the polymer divided by the weight of the polymer used. It is believed that the crosslinked polymeric ammonium salts that swell to the preferred levels have certain advantages as blood plasma cholesterol level lowering agents, such as increased capacity to sequester bile acids and soft gel texture which leads to less irritation.

By an ammonium salt or ion is meant a nitrogen atom bonded to four other atoms, for example in the ammonium ion itself, to four hydrogen atoms. In a primary ammonium ion the nitrogen atom is bonded to three hydrogen atoms and one carbon atom, in a secondary ammonium ion it is bonded to two carbon atoms and two hydrogen atoms, in a tertiary ammonium ion to three carbon atoms and one hydrogen atom, and in a quaternary ammonium ion to 4 carbon atoms. In the polymeric ammonium salts of the present invention, at least 25% of the ammonium nitrogen atoms are secondary ammonium nitrogen atoms, preferably at least about 40%. In one preferred embodiment primary ammonium nitrogen atoms are 15 to 25%, secondary ammonium nitrogen atoms are 40-60%, tertiary ammonium nitrogen atoms are 15 to 25% and quaternary ammonium nitrogen atoms are less than 5%, all of the total ammonium nitrogen atoms in the polymer. Determination of what types of ammonium nitrogen atoms are present is illustrated in Example 53.

Each nitrogen atom of an ammonium salt has one positive charge, and a counterion for the positive charge of each ammonium ion is close by. The counterion may be any negative ion whose conjugate (Bronsted) acid is capable of protonating the conjugate base of the ammonium salt. When used as a cholesterol lowering agent the counterion should be biologically compatible, that is not cause substantial undesired physiological changes. Suitable biologically compatible counterions include chloride, bromide, iodide, sulfate, phosphate, acetate, ascorbate, carbonate, bicarbonate, nicotinate, salicylate, tartrate and citrate. Chloride ion is an especially preferred counterion.

The nitrogen atoms of the ammonium salts (ions) of the polymer are located between polymer segments, unless they are end groups. At least about 25% of these groups, designated herein as Y, linking these nitrogen atoms are independently selected from n-alkylene groups having 7 to about 20 carbon atoms. By an n-alkylene group herein is meant the group —$(CH_2)_b$— wherein b in this instance is 7 to about 20. This n-alkylene group Y may also be substituted with alkyl groups, and is then in effect a branched alkylene group. It is preferred if the n-alkylene group has 7 to 14 carbon atoms, and more preferred if it has 9 to 12 carbon atoms. It is contemplated that other hydrocarbylene groups, such as ones wherein the distance between nitrogen atoms is equivalent to at least 7 methylene groups, are also operative.

The other nitrogen atoms of the ammonium salts are connected by hydrocarbylene groups, designated herein as Z, containing 2 or more carbon atoms, preferably 2 to 50 carbon atoms, that is there must be at least two carbon atoms between the nitrogen atoms. By hydrocarbylene herein is meant a divalent radical containing only carbon and hydrogen. The hydrocarbylene group Z may be substituted by various substituents. It is preferred if the hydrocarbylene group is saturated. Substituents include ether, ester amino, thioether, keto, silyl group or heterocyclic rings. Preferred substituents are ether and amino. It is preferred if the hydrocarbylene group Z is an n-alkylene group containing 2 to 14 carbon atoms. It is also preferred if the substituents contain 1 to 50 carbon atoms, more preferably 1-30 carbon atoms.

One method of preparing the instant polymeric ammonium salts is the reaction of an organic dihalide with a diamine, both of whose amine groups are primary amines. For the purposes of this discussion, the dihalide can be represented by X—Y—X and/or X—Z—X, where X is chlorine, bromine or iodine (bromine is preferred), and Y or Z is the group to which both halogen atoms are bound. The diamine is represented by $H_2N$—Y—$NH_2$ and/or $H_2N$—Z—$NH_2$, where Y or Z is the group to which the two amino groups are bound. In order to obtain the desired polymer, at least some of the dihalide and/or some of the diamine must contain Y as described above. In order to optimally obtain the desired polymer it has been found that the Y or Z group should be of such a size that the halogen atoms are the equivalent of about 7 or more methylene groups apart, that is be separated by 7 methylene groups or an equivalent distance if not separated by methylene groups. It is believed that if this minimum separation of the halogen atoms is not present, the dihalide tends to "back bite" after the first halogen has reacted with an amine, to give an undesirable cyclic structure. Thus, it is often convenient (but not necessary) that the dihalide be X—Y—X. Groups Y and Z may be selected independently at each position in a particular polymer.

Useful dihalides include, but are not limited to, 1,10-dibromodecane, 1,12-dibromododecane, 1,8-dibromooctane, 1,18-dibromooctadecane, 1,9-dibromononane, 1,7-dibromoheptane, 1,8-diiodooctane, 1,8-dibromo-3-ethyloctane, and 1,9-dibromodecane. Useful diamines include, but are not limited to, ethylene diamine, 1,6-diaminohexane, 1,12-diaminododecane, 2-methyl-1,5-diaminopentane, 1,4-bis(aminomethyl)cyclohexane, 1,3-diaminopentane, diethylenetriamine, 1,4-bis(3-aminopropyl)piperazine, 1,4-cyclohexanediamine, 5-amino-1-aminomethyl-1,3,3-trimethylcyclohexane, 1,3-propanediamine, 1,4-butanediamine, 1,5-pentanediamine, 1,7-heptanediamine, 1,8-diaminooctane, 1,9-diaminononane, 1,10-diaminodecane, 1,11-diaminoundecane, 2-hydroxy-1,3-propanediamine, and 4,4'-methylene-bis(cyclohexylamine). More than one diamine and/or dihalide may be used, so long as the limitations imposed on the polymeric structure are met, for example, at least about 25% of the total groups Y and Z should be Y.

The polymeric ammonium salts can also be made by reaction of a diamine with a diepoxide. In this case, it is the diamine in which the nitrogen atoms are connected by an n-alkylene group (which may be alkyl substituted) containing 7 to about 20 carbon atoms. See Examples 57-63 for the preparation of such sequestrants. After synthesis of these polymers, the ammonium salts are formed by neutralization of the amines with acids.

The polyamines (and their salts), as described herein, may have nitrogen atoms that are further substituted, typically by reaction with (substituted) alkyl halides to form for example, secondary amine (salts) from primary amines, and tertiary amines from secondary amines. However, in the resulting polyamine (salt), 25% or more of the amino (ammonium) nitrogen atoms should still be secondary. The group Q which is further substituted on a nitrogen is a hydrocarbyl group containing 1 to 50 carbon atoms, and may contain one or more hydroxy, ether, amino, thioether, keto, silyl groups or heterocyclic rings. It is preferred if Q contains 1–30 carbon atoms. Such polyamine salts are described in Examples 39 to 50, 69 and 70.

The polymeric ammonium salts can be made from the above diamines and dihalides or diepoxides by dissolving the reactants in a solvent, typically a polar solvent such as methanol, ethanol, N,N-dimethylformamide, N,N-dimethylacetamide, dimethylsulfoxide, tetrahydrofuran, water, and mixtures thereof. The temperatures are not critical, ambient temperatures to the boiling points of the solvent (or lower boiling ingredient) being useful. Depending on the temperature, reactants and solvent, reaction is complete in a few minutes to a few days, typically about 1 to 8 hours. The reaction may be followed by observing the viscosity of the solution, which will gradually increase until a gel is formed or the polymeric product precipitates. If the polymer does not precipitate (when it can be isolated by filtration), the polymer can be recovered from the resulting gel by adding the gel to a solvent in which the polymer is not soluble, for example tetrahydrofuran, in which the polymer will precipitate.

It is desirable in this process to use approximately equimolar amounts of the diamine and dihalide. The process is preferably carried out under an inert gas (no oxygen) blanket to avoid undesired oxidation of the amines.

If it is desired to change the counter ion of the polymer, this can be accomplished by adding a solvent to form a gel, adding a base such as ammonium hydroxide or NaOH to form a salt with the original counterion, removing the salt by washing, and then reacidifying with the conjugate acid of the counterion desired. Procedures of this type are known in the art.

In processes for preparing the polymers of the present invention, there is usually some small amount of the reactants that are polymeric but not crosslinked. If it is desired to remove this uncrosslinked (and therefore soluble) fraction, this can be done by extracting the polymeric ammonium salt with a solvent in which the uncrosslinked polymer dissolves, such as water or methanol. See for instance Example 1.

Crosslink density (as measured by the swell factor in water) can be controlled by judicious use of solvents, temperature and reaction time. Some solvents (e.g. $H_2O$, EtOH), when used alone, produce polymers that swell very little in water. Mixtures of solvents and solvents such as MeOH can produce highly swellable polymers. Short reaction times and/or lower temperatures produce less crosslinking and a higher degree of swelling.

Crosslinking can also be accomplished by using small amounts of tri- or higher functionality amines or halides (see Example 67). Crosslinking can also be accomplished by exposing the uncrosslinked polymeric ammonium salt to ionizing radiation.

In the embodiment mentioned above, when used for bile acid sequestration, the polymeric ammonium salt preferably should have a swell factor of at least about 4 in water. The degree of swellability of the polymer is determined by 3 major factors. One of these is the degree of salt formation in the polymer, that is what percentage of the amino nitrogen atoms present are in their salt form. The higher this percentage, the more the polymer will swell. It is preferred if at least 80% of the amino groups are in their salt form, and more preferred if at least about 90% are in the salt form. Included within the definition of "polymeric ammonium salt" herein is a polymer where at least about 50% of the amino groups in the polymer are in their salt form. Another factor controlling swellability is the hydrophilicity of the groups between nitrogen atoms. Generally, the more carbon atoms these groups contain, the less hydrophilic they are, and the less the polymer will swell in water. The final controlling factor is crosslink density. Typically, the higher the crosslink density, the less the polymer will swell.

The conditions during polymer synthesis and handling affect these factors. Thus, swell increases with decreasing monomer concentration in the reaction solution, undergoing a sharp increase at high dilution. The reaction time is also important. The reactants react to form higher molecular weight polymer at longer incubation times. Reaction temperature contributes to MW growth, with elevated reaction temperatures producing higher molecular weight (more crosslinks) in shorter periods of time. The workup procedure also removes low molecular weight polymer and decreases swell. Washing the product with aqueous base, then with acid, shrinks and reswells the polymer, squeezing out soluble components. A further reduction in swell is observed after continuously extracting the polymer with an organic solvent, followed by water, in a Soxhlet apparatus.

The choice of solvent for the polymerization has a large effect on the swellability of the final product. A swell of essentially zero is obtained in media which do not dissolve the reactants. Swell is very low in interfacial systems in which dibromodecane is dissolved in an organic phase and hexamethylenediamine in water. The swell can be increased slightly by neutralizing the acid by-product which is generated. The formation of higher swell polymers is promoted by solvents which dissolve both reactants, especially dipolar, aprotic solvents.

The polymeric ammonium salts are useful as bile acid sequestrants (which lower blood plasma cholesterol levels), moisture or solvent absorbents, electro-conductive agents, charge transfer agents, chelating agents and ion exchange resins.

As noted in the paragraph above, a utility for the crosslinked polymeric ammonium salts of the present invention is as bile acid sequestrants for lowering blood plasma cholesterol in mammals. Coronary and peripheral vascular diseases are major problems in Western society and elevated blood cholesterol levels is one of the major risk factors in the development of atheroscherosis in animals as well as in humans. Several studies using lipid-lowering agents have shown the beneficial effects of lowering cholesterol and low-density lipoprotein (LDL) cholesterol in the prevention of coronary heart disease.

The only quantitatively significant way by which the body can eliminate cholesterol is via the bile, either by excretion of the sterol in unchanged form or after its conversion into bile acids. Cholesterol is catabolized in the liver to bile acids which are transported to the intestine through the bile ducts to facilitate the uptake of dietary lipids.

About 95% of bile acids secreted to the gut are reabsorbed. A small amount of bile acids are lost and excreted with feces. The losses are compensated for by new synthesis. In animals and in man, treatment with bile acid binding resins such as cholestyramine, which bind bile acids in the intestine and prevent their reabsorption, increases fecal bile acid excretion. The increased fecal loss of bile acids is balanced by stimulation of bile acid synthesis from cholesterol in the liver, and there is a resulting decrease in plasma cholesterol levels. It has been shown that plasma cholesterol lowering after bile acid sequestrant treatment is due to increased hepatic cholesterol uptake via enhanced LDL receptor activity.

As described in the below Examples, the crosslinked polymeric ammonium salts of the present invention efficiently bind bile acids and are effective in lowering plasma cholesterol levels when administered to animals.

Also included in the present invention are pharmaceutically acceptable salts and prodrugs of the above-described crosslinked polymeric ammonium salts. As used herein, "pharmaceutically acceptable salts and prodrugs" refer to derivatives of the disclosed compounds that are modified by making acid salts, or by modifying functional groups present in the compounds in such a way that the modifications are cleaved, either in routine manipulation or in vivo, to the parent compounds. Examples include, but are not limited to acetate, formate and benzoate derivatives and the like.

Pharmaceutically acceptable salts of the compounds of the invention can be prepared by reacting the free base forms of these compounds with a stoichiometric amount of the appropriate acid in water or in an organic solvent, or in a mixture of the two. Lists of suitable salts are found in *Remington's Pharmaceutical Sciences*, 17th ed., Mack Publishing Company, Easton, Pa., 1985, p. 1418, the disclosure of which is hereby incorporated by reference.

DOSAGE AND FORMULATION

The bile acid sequestrant polymers of the invention can be administered as cholesterol lowering agents by any means that produces contact of the active agent with bile acids in the gut of a mammal. The bile acid sequestrant polymers of the invention are preferably administered orally, and are administered either as individual therapeutic agents or in combination with other therapeutic agents, such as with other hypocholesterolemic agents and other drugs for the treatment of cardiovascular diseases. They can be administered alone, but generally administered with a pharmaceutical carrier selected on the basis standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient may be, for example, an oral dose of about 0.1 to 10 grams being administered 1–4 times a day. The bile acid sequestrant polymers of the invention may be administered for a period of continuous therapy of one month or more, sufficient to achieve the required lowering in serum cholesterol levels.

Dosage forms (compositions suitable for administration) contain from about 0.1 gram to about 10 grams of active ingredient per unit. In these pharmaceutical compositions the active ingredient will ordinarily be present in an amount of about 20–95% by weight based on the total weight of the composition.

The active ingredient can be administered orally in solid dosage forms, such as capsules, tablets, and powders, or in liquid dosage forms, such as elixirs, syrups, and suspensions. Formulation of dosage forms of the polymers of the present invention must take into account the swelling of the particular polymers by water or other solvents.

The polymers of the invention can also be incorporated in a variety of solid foods such as bread, cookies, cake, cereals, desserts, and the like.

The polymers of the invention may be administered in tablet or in gelatin capsules containing solid bile acid sequestrant polymer or an aqueous or semi-aqueous suspension of solid polymer containing a suitable suspending agent. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastro-intestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers. Antioxidizing agents such as sodium bisulfite, sodium sulfite, or ascorbic acid, either alone or combined, are suitable stabilizing agents. Also used are citric acid and its salts and sodium EDTA. In addition, solutions can contain Pat. No. preservatives, such as benzalkonium chloride, methyl- or propyl-paraben, and chlorobutanol.

The pharmaceutical compositions of the present invention can be prepared by techniques known to those skilled in the art of pharmacy. Suitable pharmaceutical carriers and formulations are described in *Remington's Pharmaceutical Sciences*, Mack Publishing Company, a standard reference text in this field.

Useful pharmaceutical dosage forms for administration of the polymers of this invention can be illustrated as follows:

Capsules

A large number of unit capsules are prepared by filling standard two-piece hard gelatin capsules each with 0.5 gram of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 0.5 gram of the active ingredient. The capsules are washed and dried.

Tablets

A large number of tablets are prepared by conventional procedures so that the dosage unit is 0.5 gram of active ingredient, 0.2 milligrams of colloidal silicon dioxide, 0.5 gram of magnesium stearate, 275 milligrams of microcrystalline cellulose, 11 milligrams of starch and 98.8 milligrams of lactose. Appropriate coatings may be applied to increase palatability or delay absorption. Suspenion: An aqueous suspension is prepared for oral administration so that each dose contains 500 milligrams of finely divided gelled active ingredient, 200 milligrams of sodium carboxymethyl cellulose, 5 milligrams of sodium benzoate, 1.0 grams of sorbitol solution, U.S.P., and 0.025 milliliters of vanillin.

In the following examples, MeOH is methanol, EtOH is ethanol, DMAC is N,N-dimethylacetamide and DMF is N,N-dimethylformamide.

DETERMINATION OF POLYMER SWELL FACTOR

Into a pre-dried, rated, 150 mL coarse fritted filter funnel is added about 1 g of polymer. The stem of the funnel is sealed with a rubber stopper. The funnel is placed on a filter flask and about 100 mL of distilled water at about 25° C. is added to the funnel. The contents are stirred, if necessary, to fully disperse the water and polymer. The contents are then left undisturbed for 15 minutes. The rubber stopper is then removed from the stem of the funnel, suction is applied to the funnel for 5 minutes. The stem and underside of the funnel are then rinsed with ethanol to remove any remaining water droplets and suction is then continued for an additional 5 minutes. Any remaining water droplets are wiped off the funnel with a paper towel. The funnel and contents are then weighed to determine the weight of water retained by the polymer.

| | |
|---|---|
| Swell Factor | = (Total wt. of wet polymer + funnel) − (Total wt. of dry polymer + funnel) /wt. of dry polymer.<br>= wet wt. − dry wt./dry wt.<br>= g water retained/g polymer |

EXAMPLE 1

All polymers were prepared under similar conditions. The following procedure illustrates the method used. Into a 1 L three-necked flask equipped with a heating mantle, reflux condensor, overhead stirrer, and nitrogen inlet was added 130 ml of DMF, 130 ml of MeOH, 46.4 g (0.40 mole) of hexamethylene diamine, and 120.0 g (0.40 mole) of 1,10-dibromodecane. The resulting homogeneous solution was stirred rapidly and heated to reflux. After 0.5–3 hours of reflux the entire contents of the flask became a swollen gelled mass. The stirring was stopped and the flask was gently heated for an additional 18–21 hours. After heating, the gel was allowed to cool to room temperature and was scooped out of the reaction vessel. The gel was then put into a Waring Blender with an equal volume of tetrahydrofuran (THF) and was ground in the blender. This procedure was repeated at least 3 times with filtration between each chopping. The resulting washed polymer was then put into a vacuum oven set at 50°–120° C. for a period of 1–3 days to affect drying. Dry weight was 160 g (96%). To insure purity, the polymer was then Soxhlet extracted with methanol for 3.5 days and with water for an additional 3.5 days. During this process approximately 30% of the mass of the product was extracted into the solvents. The resulting polymer is dried under vacuum to afford a granular cream colored product. The polymer had a faint "nutty" odor.

The bromide counterion or any other counterion, can readily be exchanged by exposing swollen wet ($H_2O$) polymer to a 10% solution of ammonium hydroxide. The neutralized polymer shrinks (deswells) and is filtered and washed with water until the resulting filtrate is neutral to pH paper. The polymer is then reacidified with the appropriate acid to give the desired counter ion (e.g., HCl for Cl-ion; HOAc for acetate ion; etc.). Upon reacidification, the polymer swells again. The swollen polymer is then washed with water until the filtrate is neutral to pH paper and dried under vacuum to yield a granular polymer with a different counter ion.

Examples 2–38, Table 1, were carried out in a similar manner to Example 1. Reflux and heating times were the same as in Example 1.

TABLE 1

Preparation of Polyamine Salts

| Example | Ingredients (wt. g) | Solvent (vol. ratio) | Total Solvent (mL) | Temperature °C. | Final Counterion | Polymer Yield (g) |
|---|---|---|---|---|---|---|
| 2 | 1,4-bis(3-aminopropyl)piperazine (80.0)<br>1,10-dibromodecane (120.0) | DMF-MeOH<br>(1:1) | 260 | reflux | Br | 91.9[a] |
| 3 | hexamethylenediamine (46.4)<br>1,10-dibromodecane (120.0) | MeOH | 260 | reflux | Br | 164.2[b] |
| 4 | 1,12-diaminodecane (30.0)<br>1,12-dibromodecane (49.2) | DMF-MeOH<br>(1:1) | 120 | reflux | Br | 52.5[a] |
| 5 | hexamethylenediamine (45.4)<br>1,10-dibromodecane (120.0) | water | 260 | reflux | Br | 108.3[b] |
| 6 | 1,4-cyclohexane bis(methylamine) (28.4)<br>1,10-dibromodecane (60.0) | DMF-MeOH<br>(1:1) | 150 | reflux | Br | 86.6[b] |
| 7 | 4,4'-methylenebis(cyclohexylamine) (42.0)<br>1,10-dibromodecane (60.0) | DMF-MeOH<br>(1:1) | 150 | reflux | Br | 97.5[b] |
| 8 | 2-methyl-1,5-pentanediamine (23.2)<br>1,10-dibromodecane (60.0) | DMF-MeOH<br>(1:1) | 140 | reflux | Br | 73.2[b] |
| 9 | cis and trans-1,4-diaminocyclohexane (22.8)<br>1,10-dibromodecane (60.0) | DMF-MeOH<br>(1:1) | 140 | reflux | Br | 75.9[b] |
| 10 | hexamethylenediamine (46.4)<br>1,10-dibromodecane (120.0) | DMF-MeOH<br>(1:1) | 260 | RT | Br | 152.5[b] |
| 11 | ethylenediamine (12.0)<br>1,10-dibromodecane (60.0) | DMF-MeOH<br>(1:1) | 140 | reflux | Br | 40.5[b] |
| 12 | metheneamine (14.0)<br>1,10-dibromodecane (30.0) | DMF-MeOH<br>(1:1) | 70 | RT | Br | 24.4[b] |
| 13 | t-1,4-cyclohexanediamine (22.8)<br>1,10-dibromodecane (60.0) | DMF-MeOH<br>(1:1) | 140 | reflux | Br | 59.7[b] |
| 14 | isophoronediamine (17.0)<br>1,1-dibromodecane (30.0) | DMF-MeOH<br>(1:1) | 70 | reflux | Br | 35.0[b] |
| 15 | 3,3-diamino-1,2,4-triazole (9.9)<br>1,10-dibromodecane (30.0) | DMF-MeOH<br>(1:1) | 70 | reflux | Br | 18.8[a,c] |
| 16 | 1,3-diaminopentane (10.2)<br>1,10-dibromodecane (30.0) | DMF-MeOH<br>(1:1) | 70 | reflux | Br | 41.0[b,c] |

TABLE 1-continued

Preparation of Polyamine Salts

| Example | Ingredients (wt. g) | Solvent (vol. ratio) | Total Solvent (mL) | Temperature °C. | Final Counterion | Polymer Yield (g) |
|---|---|---|---|---|---|---|
| 17 | hexamethylenediamine (5.8) 2-methyl-1,5-pentanediamine (5.8) 1,10-dibromodecane (30.0) | DMF-MeOH (1:1) | 70 | reflux | Br | 40.0[b] |
| 18 | diethylenetriamine (10.3) 1,10-dibromodecane (30.0) | DMF-MeOH (1:1) | 70 | reflux | Br | 25.2[a] |
| 19 | 2-methyl-1,5-pentanediamine (11.6) 1,10-dibromodecane (30.0) | DMF-MeOH (1:1) | 70 | RT | Br | 37.3[b] |
| 20 | t-1,4-diaminocyclohexane (5.7) hexamethylenediamine (5.8) 1,10-dibromodecane (30.0) | DMF-MeOH (1:1) | 70 | reflux | Br | 40.2[b] |
| 21 | cis- and trans-1,4-diaminocyclohexane (5.7) hexamethylenediamine (5.8) 1,10-dibromodecane (30.0) | DMF-MeOH (1:1) | 70 | reflux | Br | 37.9[b] |
| 22 | t-1,4-diaminocyclohexane (5.7) isophoronediamine (8.5) 1,10-dibromodecane (30.0) | DMF-MeOH (1:1) | 70 | reflux | Br | 40.7[b] |
| 23 | dimer diamine (30.0)[d] 1,10-dibromodecane (15.0) | DMF-MeOH (1:1) | 80 | reflux | Br | 36.3[b] |
| 24 | hexamethylenediamine (278.4) 1,10-dibromodecane (720) | DMF-MeOH (1:1) | 1560 | reflux | Br | 993.7[b] |
| 25[e] | polymer of Example 1 (10.0) | | | | Cl | 5.59 |
| 26[e] | polymer of Example 24 (176) | | | | Cl | 92.2[a] |
| 27 | hexamethylenediamine (3.48) 1,10-dibromodecane (9.0) | DMAC-MeOH-water 58:8:34 | 20 | reflux | Cl | 5.38[a] |
| 28 | hexamethylenediamine (3.87) 1,10-dibromodecane (12.6) | DMF-MeOH (1:1) | 24 | reflux | Cl | 8.4[a] |
| 29 | hexamethylenediamine (3.48) 1,10-dibromodecane (9.0) | MeOH-water (1:1) | 20 | 60 | Cl | 3.7[b] |
| 30 | hexamethylenediamine (3.48) 1,10-dibromodecane (9.0) | DMAC-MeOH (3:1) | 20 | 85 | Cl | 6.54[a] |
| 31 | hexamethylenediamine ((3.48) 1,10-dibromodecane (9.0) | DMAC-MeOH-water (66:17:17) | 20 | 84 | Cl | 5.35[a] |
| 32 | 1,8-diaminooctane (4.8) 1,10-dibromodecane (10.0) | DMF-MeOH (1:1) | 24 | reflux | Cl | 7.2[a] |
| 33 | 1,12-diaminododecane (6.66) 1,10-dibromodecane (10.0) | DMF-MeOH (1:1) | 24 | reflux | Cl | 8.7[a] |
| 34 | 1,7-diaminoheptane (4.33) 1,10-dibromodecane (10.0) | DMF-MeOH (1:1) | 24 | reflux | Cl | 6.6[a] |
| 35 | 1,4-diaminobutane (2.93) 1,10-dibromodecane (10.0) | DMF-MeOH (1:1) | 24 | reflux | Cl | 5.1[a] |
| 36 | 5,5'-methylenedifurfurylamine (2.5) 1,10-dibromodecane (3.65) | DMF-MeOH (1:1) | 12 | reflux | Cl | 3.1[b] |
| 37 | hexamethylenediamine (46.4) 1,10-dichlorodecane (84.4) | MeOH | 260 | reflux | Cl | 123.7[b] |
| 38 | 1,3-diamino-2-hydroxypropane (3.0) 1,10-dibromodecane (10.0) | DMF:MeOH (1:1) | 24 | reflux | Cl | 2.88[b] |

[a]purified polymer
[b]crude polymer
[c]gummy solid

[d]dimer diamine is $H_2N(CH_2)_n(CH_2CH)_m(CH_2)_{16-m-n}$

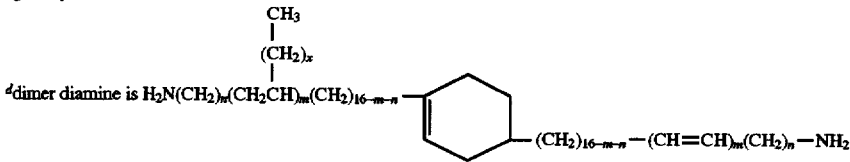

$-(CH_2)_{16-m-n}-(CH=CH)_m(CH_2)_n-NH_2$

[e]change of counterion from Br to Cl

EXAMPLES 39–50

PREPARATIONS OF SUBSTITUTED POLYMERS

All polymers were prepared in a similar manner. Polyamine was first synthesized and then used in all subsequent reactions. Polymer was synthesized as in Example 1 and was stirred in 3 L of water until it was completely swollen (about 1 hour). At that time 400 ml of conc. ammonium hydroxide was added to the swollen polymer slurry and the mixture was stirred for at least 15 minutes. The product was then filtered and washed with water until the filtrate was neutral. After drying in a vacuum oven at 60° C., 54.6 g (88.7%) of polyamine was recovered.

EXAMPLE 39

Into a 100 mL three-necked round bottom flask was placed 20 mL DMF, 20 mL distilled water, 3.0 g of the polyamine prepared above and 2.32 g of 1-bromooctane. The mixture was refluxed at least 18 hours, after which time the contents of the flask were poured into 100 mL THF and stirred for 30 min. At this point, the product could be dried and weighed to determine extent of polymer substitution. The product was then added to 100 mL of a 10% HBr/water solution, stirred for at least 30 min., filtered, and washed with water until the filtrate was neutral to pH paper. The resulting polymer was then dried in a vacuum oven. The final yield of substituted polymer was 5.65 g (88.8%).

The following polymers were prepared in an identical manner using the following ingredients and quantities. See Table 2.

HCl (4 L conc. HCl+6 L water). The polymer was then filtered and washed with distilled water until the filtrate was neutral. The polymer was then washed with methanol and slurried in methanol. The slurried polymer was then loaded into 5 L Soxhlet extraction thimbles and extracted with methanol for 3–4 days and with water for an additional 3–4 days. The polymer was then removed from the extraction thimbles and dried in a vacuum oven at 60° C. for 2–3 days to yield the final polyammonium product containing chloride counter ion. Theoretical yield was 1089 g. Yield before

TABLE 2

| Example | Ingredients | Ing. Wt. (g) | Intermediate Wt. (g) | Polymer Final Wt. (g) |
|---|---|---|---|---|
| 40 | 2-(2-bromoethyl)-1,3-dioxane | 3.81 g | | |
| | polyamine | 5.0 g | — | 3.1 g |
| 41 | 2-(2-bromoethyl)-1,3-dioxolane | 3.53 g | | |
| | polyamine | 5.0 g | — | 8.24 g |
| 42 | BrCH$_2$CH$_2$OCH$_2$CH$_2$OCH$_2$CH$_2$OCH$_3$ | 1.62 g | | |
| | polyamine | 1.83 g | 2.79 g | 3.04 g |
| 43 | 1-bromohexadecane | 2.38 g | | |
| | polyamine | 2.0 g | 3.69 g | 3.9 g |
| 44 | 2-bromotridecane | 1.98 g | | |
| | polyamine | 2.0 g | 3.3 g | 3.65 g |
| 45 | 2-(bromoethyl)tetra-hydro-2H-pyran | 1.40 g | | |
| | polyamine | 2.0 g | 2.4 g | 2.88 g |
| 46 | 1-bromoundecane | 1.84 g | | |
| | polyamine | 2.0 g | 3.37 g | 3.73 g |
| 47 | 2-bromoeicosane | 2.82 g | | |
| | polyamine | 2.0 g | 3.82 g | 4.08 g |
| 48 | 1-bromooctadecane | 2.60 g | | |
| | polyamine | 2.0 g | 3.91 g | 4.25 g |
| 49 | 2-bromoethylmethylester | 1.08 g | | |
| | polyamine | 2.0 g | 2.41 g | 2.80 g |
| 50 | 2-bromoethylethylether | 1.20 g | | |
| | polyamine | 2.0 g | 2.46 g | 2.94 g |

EXAMPLE 51

PREPARATION OF LARGE QUANTITY OF POLYMER

Into a 5 L three-necked round bottom flask equipped with an ice bath, overhead stirrer, reflux condenser, thermometer, and nitrogen inlet were added 1 L of DMF, 1 L of methanol, 386.7 g (3.33 mol) of hexamethylene diamine, and 1000.0 g (3.33 mol) of 1,10-dibromodecane. The resulting homogeneous solution was rapidly stirred without heating. Within 10 minutes the solution attained a temperature of 82° C. and refluxing occured. At this time ice was added to the ice bath to maintain a steady rate of reflux. After 20 minutes the initial heat of reaction dissipated and refluxing stopped. At this time, the ice bath was removed and a heating mantle was placed on the flask. The flask was then heated to maintain a steady reflux of the solvents. As the reaction solution was heated and stirred rapidly the viscosity of the reaction began to increase. Within 20 to 30 minutes after the beginning of heating the reaction, the mixture attained a viscosity which no longer allowed stirring. At this point, the agitator was stopped. The resulting swollen gelled mass was then gently heated at 30° C.–50° C. for an additional 18 to 21 hours. The gel was allowed to cool to room temperature and was scooped out of the reaction vessel. The gel was then put into a blender with an equal volume of 10% aqueous ammonium hydroxide and was ground in the blender. The resulting polymer was filtered and then slurried in 10% aqueous ammonium hydroxide for 1 hour. The polymer was then filtered and washed with distilled water until the filtrate was neutral. The polymer was then treated with 10 L of aqueous extraction was 823 g. Yield after extraction was 800 g. The polymer could be ground in a blender or coffee mill to yield particle sizes of 30–500 microns. High speed hammer milling through a 100 mesh screen produced particle sizes in the range of 30–150 microns. Air jet micronizing produced particle sizes in the range of 30–150 microns. Grinding in an attritor in the presence of liquid nitrogen produced particle sizes as low as 1 micron. In most cases the material was coffee milled before use.

EXAMPLE 52

SWELLING OF POLYMER PRODUCED IN EXAMPLE 1 (Br$^-$ ION)

To 0.5 g polyammonium bromide prepared in Example 1 was added 13 mL of distilled water. Within minutes the polymer swelled to completely absorb that volume of water. When the vial was inverted no liquid water poured. This behavior indicates at least a 26:1 (2600%) swell factor for this polymer.

EXAMPLE 53

DETERMINATION OF EXTENT OF BRANCHING/CROSSLINKING OF POLYMER PRODUCED AS IN EXAMPLE 1 (Br$^-$ ION)

Polyammonium bromide prepared as described in Example 1 was placed in a 10 ad NMR tube. To this was added enough dioxane to slurry the polymer. Water (D$_2$O) was then added to swell the polymer. A $^{13}$C NMR spectra was then run on the sample. The following signals were observed for the carbon atoms immediately adjacent to the different possible nitrogen species contained in the polymer structure. 40.10 ppm (—C—$NH_3^+$) (10.24 integral units); 48.27 ppm (—C—$NH_2^+$—C—) (52.22 iu); 53.48 ppm

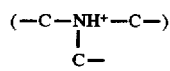

(35.07 iu); 58.75 ppm

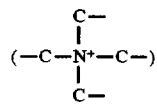

(2.57 iu). Relative nitrogen abundance could be calculated as follows:

| | | |
|---|---|---|
| primary N (40.10 ppm) = | 10.24/1 = 10.24 | 21.0% |
| secondary N (48.27 ppm) = | 52.22/2 = 26.11 | 53.6% |
| tertiary N (53.48 ppm) = | 35.07/3 = 11.69 | 24.0% |
| quaternary N (58.75 ppm) = | 2.57/4 = 0.64 | 1.3% |

Thus, this polymer contained 53.6% secondary (straight chain) amines, 24.0% tertiary amines as either branch points or crosslinks, 21.0% primary amines as ends, and 1.3% quaternary amines as crosslinks or branch points.

In Vitro Binding of Bile Acids to Bile Acid Sequestrants

The binding of bile acids to the bile acid sequestrant crosslinked polymeric ammonium salts of the present invention may be measured using the procedures described below.

The following method was used to measure the equilibrium binding paramaters for the binding of various bile acids to the bile acid sequestrants of the present invention. The equilibrium binding of bile acids to bile acid sequestrants was determined using isotonic ionic conditions at 37° C., in order to roughly approximate physiological conditions. Carbon-14 ($^{14}C$) labeled bile acids dissolved in phosphate buffered saline (PBS) at pH 7 were prepared at 0.454, 0.555, 0.713, 1.000, 1.667, 5.000, 6.667, 10.0, 20.0 and 30.0 mM (45 nCi $^{14}C$/ml) concentrations. This series of reciprocal concentration levels were chosen to afford relatively even distribution of empirical data along the semilogarithmic saturation binding curves.

The bile acids were purchased from Sigma (St. Louis, Mo.) and the $^{14}C$ labeled bile salts having a specific activity of approximately 50 mCi/mmole were obtained from E. I. du Pont de Nemours and Company, New England Nuclear (Billerica, Mass.).

Two mL of the prepared concentrations of bile acid were added to a selected amount (for example, 5.0 mg) of bile acid sequestrant to be tested, within a 10,000 mw cut-off ultrafiltration cup (Nihon Millipore, Yonezawa, Japan) and incubated overnight (16 hours) at 37° C.

Cholestyramine, which was tested for reference, was obtained from Sigma, St. Louis, Mo.

To determine the non-specific binding, the ten stock solutions of bile salts were added to empty ultrafiltration cups and incubated together with the total binding samples.

To separate bound and free bile acid the ultra-filtration cups were centrifuged at 3,500 RPM at 37° C. in a Du Pont RT6000 centrifuge to pass the solution of free bile acids into the outer tube. Two hundred µL of the separated binding tubes and the corresponding set of the stock solutions of total bile acid were counted for two minutes in a beta scintillation counter (Beckman, Palo Alto, Calif.) to detect $^{14}C$ DPMs in 7 mLs of Formula 989 scintillation cocktail (E. I. du Pont de Nemours and Company, New England Nuclear, Billerica, Mass.).

The respective specific bound DPMs were determined from the counted total added $^{14}C$ DPMs and derived total binding and non-specific binding DPMs. The specific bound DPMs were converted to specifically bound µmoles of bile salts at each dose level. The specific binding data was plotted on a saturation binding curve (specific bound µmoles of bile salts/mg of sequestrant versus the log of the free µmoles of bile salts/mL of solution) and the best-fit regression curve was determined using the relationship:

$$[Bound]=(Bmax \times [Free]^n)/((Kd)^n+[Free]^n)$$

where Bmax is the maximum amount of bile salt bound to sequestrant, Kd is the concentration of free bile salt at which there is half-maximal binding (i.e., an equilibrium dissociation constant) and n is a curve fitting parameter.

Data for the binding of various bile acids to representative bile acid sequestrant polymers of the present invention is shown in Tables 3 and 4 below. In Tables 3 and 4, Bmax is presented in units of µmol of bile salt bound per mg of bile acid sequestrant and Kd is in units of mM.

The value Bmax/Kd is a measure of the binding efficiency of the bile acid sequestrant for the binding of bile acids, and reflects both the total number of binding sites or binding capacity and the binding affinity of the bile acid sequestrant for bile acid. The higher this number is, the more effective a bile acid sequestrant is predicted to be.

As shown in Tables 3 and 4, the bile acid sequestrant polymers of the present invention are substantially more effective in binding bile acids, in terms of both increased affinity and increased binding capacity, relative to cholestyramine.

TABLE 3

In Vitro Equilibrium Binding of Bile Acids to Bile Acid Sequestrants

| Polymer of Ex. No. | Bile Acid | Bmax | Kd | Bmax/Kd |
|---|---|---|---|---|
| Cholestyramine | cholate | 3.38 | 7.35 | 0.46 |
| | taurocholate | 2.84 | 2.15 | 1.32 |
| | glycocholate | 2.93 | 7.38 | 0.40 |
| | chenodeoxycholate | 3.13 | 0.494 | 6.34 |
| 1 | cholate | 4.37 | 2.25 | 1.94 |
| | taurocholate | 4.62 | 1.78 | 2.60 |
| | glycocholate | 3.89 | 1.84 | 2.11 |
| | chenodeoxycholate | 3.25 | 0.163 | 19.9 |
| 37 | cholate | 5.13 | 1.47 | 3.49 |
| | taurocholate | 4.82 | 1.27 | 3.80 |
| | glycocholate | 5.11 | 1.84 | 2.78 |
| | chenodeoxycholate | 4.49 | 0.201 | 22.3 |
| 8 | cholate | 4.70 | 1.16 | 4.05 |
| | taurocholate | 4.18 | 1.38 | 3.03 |
| | glycocholate | 3.83 | 1.60 | 2.39 |
| | chenodeoxycholate | 4.77 | 0.380 | 12.6 |
| 9 | cholate | 4.16 | 2.81 | 1.48 |
| | taurocholate | 4.06 | 3.40 | 1.19 |
| | glycocholate | 4.22 | 3.76 | 1.12 |
| | chenodeoxycholate | 3.81 | 0.193 | 19.7 |

TABLE 3-continued

In Vitro Equilibrium Binding of Bile Acids to Bile Acid Sequestrants

| Polymer of Ex. No. | Bile Acid | Bmax | Kd | Bmax/Kd |
|---|---|---|---|---|
| 11 | cholate | 3.85 | 1.80 | 2.14 |
|  | taurocholate | 3.23 | 3.45 | 0.94 |
|  | glycocholate | 3.39 | 3.94 | 0.86 |
|  | chenodeoxycholate | 3.20 | 0.125 | 25.6 |
| 40 | cholate | 3.42 | 1.92 | 1.78 |
|  | taurocholate | 2.97 | 1.49 | 1.99 |
|  | glycocholate | 2.96 | 2.19 | 1.35 |
|  | chenodeoxycholate | 3.19 | 0.170 | 18.8 |
| 41 | cholate | 3.11 | 1.88 | 1.65 |
|  | taurocholate | 2.80 | 2.80 | 1.00 |
|  | glycocholate | 2.93 | 2.20 | 1.33 |
|  | chenodeoxycholate | 3.17 | 0.227 | 14.0 |
| 48 | cholate | 4.65 | 2.25 | 2.07 |
|  | taurocholate | 3.83 | 1.92 | 1.99 |
|  | glycocholate | 3.65 | 2.38 | 1.53 |
|  | chenodeoxycholate | 4.17 | 0.165 | 25.3 |

TABLE 4

In Vitro Binding of Cholate to Bile Acid Sequestrants

| Polymer of Example | Swell Factor | Bmax | Kd | Bmax/Kd |
|---|---|---|---|---|
| Cholestyramide |  | 3.38 | 7.35 | 0.46 |
| 24 | 14.4 | 4.33 | 1.43 | 3.03 |
| 25 |  | 4.51 | 1.33 | 3.39 |
| 26 | 21.6 | 4.45 | 1.19 | 3.74 |
| 27 | 2.6 | 1.70 | 1.45 | 1.17 |
| 28 | 4.9 | 4.98 | 1.11 | 4.49 |
| 29 | 1.3 | 2.33 | 1.13 | 2.06 |
| 30 | 14.6 | 5.20 | 1.29 | 4.03 |
| 32 | 12.1 | 5.34 | 1.02 | 5.24 |
| 33 | 0.1 | 2.68 | 0.61 | 4.39 |
| 34 | 11.9 | 4.05 | 0.96 | 4.22 |
| 35 | 21.5 | 5.88 | 1.25 | 4.70 |
| 38 | 135.6 | 5.26 | 0.90 | 5.84 |
| 45 |  | 1.31 | 1.02 | 1.28 |
| 46 |  | 2.96 | 2.21 | 1.34 |
| 47 |  | 3.78 | 1.53 | 2.47 |
| 50 |  | 3.70 | 1.56 | 2.37 |

In Vivo Plasma Cholesterol Lowering Activity of Bile Acid Sequestrants

The in vivo plasma cholesterol lowering activity of the bile acid sequestrant polymers of the present invention were evaluated in the animal models described below.

Plasma Cholesterol Lowering in Hamsters Administered Bile Acid Sequestrants

The plasma cholesterol lowering effect of representative bile acid sequestrant polymers of the present invention is shown in Table 5 below. Male hamsters were fed for 2 weeks the selected bile acid sequestrant to be tested and the total cholesterol concentration in the plasma was determined. Total serum cholesterol was measured using a cholesterol oxidase assay on a Dimension® clinical analyzer. The sequestrants were given orally by mixing in the animal feed. The hamsters were given 11 g of Agway rodent chow per day for 2 weeks that contained varying weights of sequestrant. Results for 0.25, or 0.3 weight % sequestrant (for example 0.3 weight % is 0.033 g sequestrant per 11 g of feed are shown). The polymer was ground and mixed with the feed.

In each study, 7 animals were dosed with the sequestrant. The % decrease in cholesterol levels was calculated by subtracting the average total cholesterol levels at 2 weeks of sequestrant treatment, from the average total cholesterol levels in the animals before treatment (week 0).

In Table 5, where a single 7 animal study was carried out, the uncertainty in the measured cholesterol lowering is expressed as the SEM (or standard deviation (SD)) for a particular study (i.e., for 7 animals). In Table 5, the SEM (or SD) for the study at Week 0 and Week 2 is given and the SEM (or SD) is also expressed as a % of the average value of total cholesterol. Also given in Table 5 is the % decrease in total cholesterol level and the average % SEM (or SD) for Weeks 0 and 2.

TABLE 5[a]

Plasma Cholesterol Lowering in Hamsters by Bile Acid Sequestrants

| Polymer of Example | Dose (weight %) | Total Cholesterol (mg/dl) (±SEM or SD) | | | | % Decrease in Total Cholesterol | Avg % Error |
|---|---|---|---|---|---|---|---|
| | | Week 0 | % Error | Week 2 | % Error | | |
| Cholestyramine | 0.3 | 171 ± 11* | ±6.4 | 150 ± 13* | ±8.7 | 12 | ±7.6* |
| 1 | 0.25 | 178 ± 4 | ±2.2 | 129 ± 3 | ±2.3 | 28 | ±2.3 |
| 1 | 0.3 | 167 ± 16* | ±9.6 | 127 ± 8* | ±6.3 | 24 | ±8.0* |
| 37 | 0.25 | 178 ± 7 | ±3.9 | 122 ± 2 | ±1.6 | 31 | ±2.8 |

[a]The total cholesterol levels are the average values for 7 animals. The value following ± is the standard error of the mean (SEM) except where marked with asterisk (*), where it is a standard deviation (SD).

Cholesterol Lowering in Rabbits Treated with Bile Acid Sequestrant

The cholesterol lowering efficacy of the polymer of Example 25 was tested in male New Zealand rabbits. As shown in Table 6 below, following 1 week and 2 weeks of treatment of rabbits with this polymer at 250 mg/kg of total body weight per day, the plasma total cholesterol levels in the animals were significantly decreased.

Table 6 shows the mean % decrease in total plasma cholesterol levels for 5 animals (the SEM is given following ±). The bile acid sequestrant was administered by being mixed with the animal feed and being fed to the animals. Total serum cholesterol was measured using a cholesterol oxidase assay on a Dimension clinical analyzer.

TABLE 6

Rabbit Plasma Cholesterol Lowering After 1 Week and 2 Weeks of Bile Acid Sequestrant Treatment

| | % Decrease in Total Cholesterol (±SEM) | |
|---|---|---|
| | 1 Week | 2 Weeks |
| no bile acid sequestrant | 7 ± 10 | 17 ± 8 |
| cholestyramine | 14 ± 11 | 17 ± 13 |
| Polymer of Example 25 | 43 ± 11 | 42 ± 10 |

In the present disclosure it should be understood that the specified materials and conditions are important in practicing the invention but that unspecified materials and conditions are not excluded from the present invention, so long as they do not prevent the benefits of the invention from being realized.

EXAMPLES 54 TO 73

Sequestrant polymers were made by a procedure similar to that used in Example 1. The starting materials and synthesis conditions are given in Table 7.

BINDING ABILITY OF THE SEQUESTRANTS OF EXAMPLES 54 TO 73

The efficacy of these sequestrants was tested using the "Sequestrant Glycocholate Binding Assay", the procedure for which is given below. In Table 8 the results of this assay are given for the sequestrants of Examples 54 to 73. The higher the "% Bound Glycocholate", the better the efficacy of the sequestrant. For comparison purposes, results from Cholestyramine and a sequestrant similar to that of Example 25 are also given.

SEQUESTRANT GLYCOCHOLATE BINDING ASSAY

A. Initial Binding Assay Each polymer was weighed directly into a Millipore® ultra filtration cup (10,000 NML low binding cellulose). The weight added to each cup was around 5 mg/cup with the actual weight being recorded and each polymer was weighed into 3 cups. A 10 mM glycocholic acid solution (GC) was made with phosphate buffered saline (PBS) at a pH of 7, and kept at 37° C. To each cup, 2 ml of the above solution was added. This was done in sets of no more than 15 cups. Once the bile acid was added to the cups the cups were mixed with a vortex mixer and placed in a centrifuge. The cups were spun in a Sorvall® RT6000 centrifuge at 3500 RPM (setting #10) at 37° C. for 10 minutes.

B. 18 Hour Assay

Each polymer was weighed directly into the Millipore ultra filtration cups (10,000 NML low binding cellulose). The weight added to each cup was around 5 mg/cup with the actual weight being recorded and each polymer was weighed into 3 cups. A 10 mM glycocholic acid solution (GC) was made with phosphate buffered saline (PBS) at a pH of 7. To each cup, 2 mL of the above solution was added. The cups were incubated in an orbital dry air shaker at 37° C. for between 18 to 20 hours. After incubation the cups were spun in the Sorvall RT6000 centrifuge at 3500 RPMS (setting #10) at 37° C. for 1 hour or until at least 200 µl of solution had been eluted.

The reagents were bought as a kit from Sigma Chemical Co., St. Louis, Mo. 63178, Bile Acid Diagnostic Kit #450-A. Reagents were gently reconstituted with water, 10 ml for reagent A and 5 ml for reagent B. They were mixed by inverting, not shaking. The test reagent was maded by mixing reagent A with reagent B at a volume ratio of 4:1. For each sample 0.5 ml of the test reagent was needed. The test reagent was warmed to 37° C. by placing it in a 37° C. water bath about 15 minutes before it was needed. The assay was performed in 6 ml polypropylene test tubes. Each sample was diluted so as to be in the linear range of the assay. The bile acid salt filtrate samples and the 10 mM GC were first diluted 10 times, 100 µl plus 900 µl PBS. Each sample was done in duplicate so that for each example there were six samples. PBS was used as a zero control and the Absorbance from the average of 6 PBS samples was subtracted from all other samples. The 10 mM GC was diluted by a total factor of 50 to be at the maximum range of the assay, which is 200 µM, and six samples were tested. The samples were diluted by a total factor 40. Two hundred µl of sample was needed for the assay. Since the samples were first diluted by 10 then diluted by 4, 50 µl of diluted sample plus 150 µl of PBS was assayed. For the 10 mM GC samples, they were also diluted first by 10 and then diluted by 5, therefore 40 µl of the diluted sample and 160 µl of PBS was assayed. For the bile acid zero controls, 200 µl of PBS was assayed. At this point all samples were treated the same. The assay was performed in batches of no more than 70 tubes. The samples were placed in the 37° C. water bath. Using a repeat pipetter 0.5 ml of test reagent was added to each tube at a consistent pace. The timer was started at the same time that the test reagent was added to the first tube. After 5 minutes the reaction was stopped by adding 100 µl of 1.33M phosphoric acid at the same pace that the test reagent was added. The samples were poured into 1.5 ml plastic cuvets and read on a spectrometer at 530 nm. Samples were only stable for one hour.

Using absorbance data obtained from standard GC solutions, the percent of bile acid bound per 5 mg of sequestrant was calculated. Cholestyramine was tested in every assay as a control. The binding assay for a polymer was repeated if the three samples were not close to each other.

TABLE 7

| Ex. No. | Composition | Wt (g) | Solvent (Vol. ratio) | Total Solvent (mL) | Temp | Final Counter Ion | Polymer Yield (g) |
|---|---|---|---|---|---|---|---|
| 54 | 1,9-Dibromonane<br>1,4-Diaminobutane | 11.08<br>3.41 | DMAC/MeOH<br>1:1 | 26 | reflux | Cl⁻ | 6.19 |
| 55 | 1,11-Dibromoundecane<br>1,4-Diaminobutane | 11.07<br>3.10 | DMAC/MeOH<br>1:1 | 21 | reflux | Cl⁻ | 7.12 |
| 56 | 1,12-Dibromododecane<br>1,4-Diaminobutane | 11.07<br>2.97 | DMAC/MeOH<br>1:1 | 21 | reflux | Cl⁻ | 4.79 |
| 57 | 1,3-Butadiene Diepoxide<br>1,8-Diaminooctane | 3.98<br>6.68 | MeOH | 11 | reflux | Cl⁻ | 10.34 |
| 58 | 1,3-Butadiene Diepoxide<br>1,9-Diaminononane | 3.81<br>7.00 | MeOH | 11 | reflux | Cl⁻ | 10.14 |
| 59 | 1,3-Butadiene Diepoxide<br>1,10-Diaminodecane | 3.44<br>6.88 | MeOH | 10 | reflux | Cl⁻ | 9.81 |
| 60 | 1,2,7,8-Diepoxyoctane<br>1,8-Diaminooctane | 4.37<br>4.42 | MeOH | 13 | reflux | Cl⁻ | 8.50 |
| 61 | 1,2,7,8-Diepoxyoctane<br>1,10-Diaminodecane | 3.70<br>4.47 | MeOH | 10 | reflux | Cl⁻ | 7.63 |
| 62 | 1,2,7,8-Diepoxyoctane<br>1,8-Dibromooctane<br>1,8-Diaminooctane | 1.17<br>6.72<br>4.74 | DMAC/MeOH<br>1:1 | 19 | reflux | Cl⁻ | 8.20 |
| 63 | 1,2,7,8-Diepoxyoctane<br>1,8-Dibromooctane<br>1,8-Diaminooctane | 2.29<br>4.37<br>4.63 | DMAC/MeOH<br>1:1 | 17 | reflux | Cl⁻ | 8.21 |
| 64 | trans-1,4-Dichloro-2-butene<br>1,8-Diaminooctane | 4.86<br>5.64 | DMAC/MeOH<br>1:1 | 16 | reflux | Cl⁻ | 6.48 |
| 65 | trans-1,4-Dichloro-2-butene<br>1,9-Diaminononane | 4.84<br>6.16 | DMAC/MeOH<br>1:1 | 16 | reflux | Cl⁻ | 7.03 |
| 66 | trans-1,4-Dichloro-2-butene<br>1,10-Diaminodecane | 4.61<br>6.39 | DMAC/MeOH<br>1:1 | 16 | reflux | Cl⁻ | 6.55 |
| 67 | 1,10-Dibromodecane<br>Tris(2-aminoethyl)amine | 7.94<br>3.84 | DMAC/MeOH<br>1:1 | 18 | reflux | Cl⁻ | 7.66 |
| 68 | 1,3-diamino-2-hydroxypropane<br>1,8-dibromooctane | 3.0<br>9.1 | DMF/MeOH<br>1:1 | 16 | reflux | Cl⁻ | 4.9 |
| 69 | hexamethylenediamine<br>hexylamine<br>1,10-dibromodecane<br>sodium carbonate | 2.9<br>0.84<br>10.0<br>3.5 | DMF/MeOH<br>1:1 | 24 | reflux | Cl⁻ | 6.7 |
| 70 | hexamethylenediamine<br>4-(aminomethyl)piperidine<br>1,10-dibromodecane<br>sodium carbonate | 1.93<br>1.90<br>10.0<br>3.5 | DMF/MeOH<br>1:1 | 24 | reflux | Cl⁻ | 7.7 |
| 71 | 1,4-butanediamine<br>2-methylpentamethylene diamine<br>1,10-dibromodecane | 1.47<br>1.93<br>10.0 | DMF/MeOH<br>1:1 | 24 | reflux | Cl⁻ | 6.3 |
| 72 | divinylbenzene<br>hexanediamine<br>1,10-dibromodecane<br>n-BuLi 1.6M (in hexane) | 5.0<br>4.46<br>3.41<br>2.26 mL | THF | 20 | reflux | Cl⁻ | 2 |
| 73 | Jeffamine ® EDR-192<br>(H₂NCH₂CH₂OCH₂CH₂OCH₂CH₂OCH₂CH₂NH₂)<br>1,10-dibromodecane<br>diethylenetriamine | 3.2<br>10.0<br>1.7 | DMF/MeOH<br>1:1 | 24 | reflux | Cl⁻ | |

TABLE 8

% BOUND GLYCOCHOLATE OF VARIOUS SEQUESTRANTS

| Polymer of Ex. No. | Swell Factor | % Bound Glycocholate |
|---|---|---|
| Cholestryamine<sup>c</sup> | — | 44–52<sup>a</sup> |
|  |  | 37–44<sup>b</sup> |
| Similar to 25<sup>d</sup> | — | 80.5<sup>a</sup> |
|  |  | 81.7<sup>b</sup> |
| 54 | 13.6 | 76.9<sup>a</sup> |
| 55 | 11.9 | 63.2<sup>a</sup> |
| 56 | 19.9 | 52.2<sup>a</sup> |
| 57 | 11.1 | 73.8<sup>a</sup> |
| 58 | 13.2 | 72.4<sup>a</sup> |
| 59 | 11.4 | 69.9<sup>a</sup> |
| 60 | 16.2 | 67.2<sup>a</sup> |
| 61 | 9.1 | 75.8<sup>a</sup> |
| 62 | 18.1 | 71.9<sup>a</sup> |
| 63 | 12.9 | 73.9<sup>a</sup> |
| 64 | 11.2 | 74.0<sup>a</sup> |
| 65 | 8.9 | 73.8<sup>a</sup> |
| 66 | 12.0 | 71.0<sup>a</sup> |
| 67 | 29.8 | 58.7<sup>a</sup> |
| 68 | 4.4 | 66.2<sup>b</sup> |
| 69 | 24.0 | 75.1<sup>b</sup> |
| 70 | 22.5 | 82.6<sup>b</sup> |
| 71 | 50.8 | 79.9<sup>a</sup> |

TABLE 8-continued

% BOUND GLYCOCHOLATE OF VARIOUS SEQUESTRANTS

| Polymer of Ex. No. | Swell Factor | % Bound Glycocholate |
|---|---|---|
| 72 | 39.1 | 80.2[b] |
| 73 | — | 60.2[a] |

[a]After 10 min.
[b]After 18 hr.
[c]Bmax (μmoles/gm) = 3.13; Kd(mM) = 7.72
[d]Bmax (μmoles/gm) = 5.83; Kd(mM) = 1.58

What is claimed is:

1. A method for lowering blood plasma cholesterol levels of mammals, comprising, orally administering a therapeutically effective amount of a crosslinked polymeric ammonium salt, wherein in said salt:

about 25% or more of the groups which link ammonium nitrogen atoms are group Y wherein Y is an n-alkylene group or alkyl substituted n-alkylene group, wherein said n-alkylene group has 7 to about 15 carbon atoms;

zero to about 75% of the groups which link ammonium nitrogen atoms are group Z, wherein Z is a hydrocarbylene radical containing 2 or more carbon atoms, said hydrocarbylene radical optionally containing one or more hydroxyl, ether, amino, thioether, keto, or silyl groups or heterocyclic rings; and about 25% or more of the ammonium nitrogen atoms are secondary ammonium nitrogen atoms.

2. A method for sequestering bile acids, comprising, contacting in an aqueous medium a bile acid and a crosslinked polymeric ammonium salt, wherein in said salt:

about 25% or more of the groups which link ammonium nitrogen atoms are group Y wherein Y is an n-alkylene group or alkyl substituted n-alkylene group; wherein said n-alkylene group has 7 to about 15 carbon atoms;

zero to about 75% of the groups which link ammonium nitrogen atoms are group Z wherein Z is a hydrocarbylene radical containing 2 or more carbon atoms, said hydrocarbylene radical optionally containing one or more hydroxyl, ether, amino, thioether, keto, or silyl groups or heterocyclic rings; and about 25% or more of the ammonium nitrogen atoms are secondary ammonium nitrogen atoms.

3. The method as recited in claim 1 or 2 wherein said Z group is saturated.

4. The method as recited in claim 1 or 2 wherein said Z is an n-alkylene group containing 2 to 14 carbon atoms.

5. The method as recited in claim 1 or 2 wherein said Y is an n-alkylene group.

6. The method as recited in claim 5 wherein said Y group contains 7 to 14 carbon atoms.

7. The method as recited in claim 6 wherein said Y group contains 9 to 12 carbon atoms.

8. The method as recited in claim 1 or 2 wherein at least about 40% of the ammonium nitrogen atoms are secondary ammonium nitrogen atoms.

9. The method as recited in claim 1 or 2 wherein 15 to 25% of the ammonium atoms are primary ammonium nitrogen atoms, 40–60% of the ammonium nitrogen atoms are secondary ammonium nitrogen atoms, 15–25% of the ammonium nitrogen atoms are tertiary ammonium nitrogen atoms, and less than 5% of the ammonium nitrogen atoms are quaternary ammonium nitrogen atoms.

10. The method as recited in claim 1 or 2 wherein a counterion is chloride, bromide, iodide, sulfate, phosphate, acetate, ascorbate, carbonate, bicarbonate, nicotinate, salicylate, tartrate or citrate.

11. The method as recited in claim 10 wherein said counterion is chloride.

12. The method as recited in claim 1 or 2 which has a swell factor in water of at least about 4.

13. The method as recited in claim 12 wherein said swell factor in water is about 5 to about 25.

14. The method as recited in claim 13 wherein said swell factor in water is about 10 to about 15.

15. The method as recited in claim 1 or 2 wherein said ammonium nitrogen atoms are further substituted with a hydrocarbyl group Q containing 1–50 carbon atoms, said hydrocarbyl group optionally containing one or more hydroxyl, ether, amino, thioether, keto, silyl groups, or heterocyclic ring.

16. The method as recited in claim 15 wherein said Q contains 1 to 30 carbon atoms.

* * * * *